(12) United States Patent
Heath et al.

(10) Patent No.: US 7,893,228 B2
(45) Date of Patent: *Feb. 22, 2011

(54) COMPOSITIONS AND METHODS FOR USING A SOLID SUPPORT TO PURIFY RNA

(75) Inventors: Ellen M. Heath, Minnetonka, MN (US); John M. Wages, Jr., Tupelo, MS (US)

(73) Assignee: Qiagen North American Holdings, Inc., Germantown, MD (US)

( * ) Notice: Subject to any disclaimer, the term of this patent is extended or adjusted under 35 U.S.C. 154(b) by 1286 days.

This patent is subject to a terminal disclaimer.

(21) Appl. No.: 09/974,798

(22) Filed: Oct. 12, 2001

(65) Prior Publication Data

US 2003/0073830 A1  Apr. 17, 2003

(51) Int. Cl.
*C07H 21/02* (2006.01)
*C08G 83/00* (2006.01)

(52) U.S. Cl. ............ 536/23.1; 536/23.2; 536/23.4; 536/23.5; 536/23.51; 536/23.52; 536/23.53; 536/23.6; 536/23.7; 536/23.71; 536/23.72; 536/23.74

(58) Field of Classification Search ........ 536/25.4, 536/25.41, 25.42, 23.1, 22.1, 23.3, 23.4, 536/23.5, 23.51, 23.52, 23.53, 23.6, 23.7, 536/23.71, 23.72, 23.74; 435/6, 91.1, 91.3, 435/375, 193, 5; 252/1
See application file for complete search history.

(56) References Cited

U.S. PATENT DOCUMENTS

| | | |
|---|---|---|
| 4,483,920 A | 11/1984 | Gillespie et al. |
| 4,843,155 A | 6/1989 | Chomczynski |
| 5,010,183 A | 4/1991 | Macfarlane |
| 5,057,426 A | 10/1991 | Henco et al. |
| 5,155,018 A | 10/1992 | Gillespie et al. |
| 5,234,809 A | 8/1993 | Boom et al. |
| 5,346,994 A | 9/1994 | Chomczynski |
| 5,405,951 A | 4/1995 | Woodard |
| 5,599,667 A | 2/1997 | Arnold, Jr. et al. |
| 5,637,687 A * | 6/1997 | Wiggins .................. 536/25.4 |
| 5,728,822 A | 3/1998 | Macfarlane |
| 5,939,259 A | 8/1999 | Harvey et al. |
| 5,945,515 A | 8/1999 | Chomczynski |
| 5,958,677 A | 9/1999 | Lee et al. |
| 5,972,613 A | 10/1999 | Somack et al. |
| 5,973,137 A * | 10/1999 | Heath .................. 536/25.4 |
| 5,985,572 A | 11/1999 | Macfarlane |
| 5,990,302 A * | 11/1999 | Kuroita et al. ............ 536/25.4 |
| 6,037,465 A | 3/2000 | Hillebrand et al. |
| 6,204,375 B1 * | 3/2001 | Lader .................. 536/25.4 |
| 6,218,531 B1 | 4/2001 | Ekenberg |
| 6,465,639 B1 | 10/2002 | van Gemen et al. |
| 6,528,641 B2 | 3/2003 | Lader |
| 6,617,170 B2 | 9/2003 | Augello et al. |
| 6,855,499 B1 * | 2/2005 | Nargessi .................. 435/6 |
| 7,115,719 B2 | 10/2006 | Paulsen |
| 7,148,343 B2 * | 12/2006 | Bair et al. .................. 536/25.4 |
| 2001/0041332 A1 | 11/2001 | Hillebrand et al. |
| 2002/0001812 A1 | 1/2002 | Smith et al. |
| 2002/0106686 A1 | 8/2002 | McKernan |
| 2002/0127587 A1 * | 9/2002 | Simms et al. .................. 435/6 |
| 2003/0092045 A1 | 5/2003 | Nargessi et al. |
| 2003/0106107 A1 | 6/2003 | Shinozaki et al. |
| 2004/0019196 A1 | 1/2004 | Bair et al. |
| 2004/0245163 A1 | 12/2004 | Lim et al. |
| 2005/0032105 A1 | 2/2005 | Bair et al. |
| 2005/0191760 A1 | 9/2005 | Heath et al. |
| 2006/0105372 A1 | 5/2006 | Bair et al. |
| 2007/0043216 A1 * | 2/2007 | Bair et al. .................. 536/25.4 |
| 2007/0092403 A1 | 4/2007 | Wirbisky et al. |

FOREIGN PATENT DOCUMENTS

| | | |
|---|---|---|
| EP | 0 818 461 | 1/1998 |
| WO | WO 92/07863 | 5/1992 |
| WO | WO 95/01359 | 1/1995 |
| WO | WO 95/02049 | 1/1995 |
| WO | WO 95/34569 | 12/1995 |
| WO | WO 96/18731 | 6/1996 |
| WO | WO99/39009 | * 8/1999 |
| WO | 2004/094635 | 11/2004 |

OTHER PUBLICATIONS

Heath et al. "Apparatus and methods for isolating nucleic acid." U.S. Appl. No. 09/154,830, filed Sep. 17, 1998.*

Calbiochem 2000/2001 catalog, published 2000 by Calbiochem Inc. p. 541 and p. 546.*

"Kosmotropes and chaotropes", http://www.isbu.ac.uk/water/kosmos.html, printed Aug. 18, 2004.

Galinski et al., "The kosmotropic (structure-forming) effect of compensatory solutes", *Comp. Biochem. Physiol.*, 117A(3), 357-365 (1997).

Lever et al., "Some ways of looking at compensatory kosmotropes and different water environments", *Comp Biochem Physiol A Mol Integr Physiol.*, 130, 471-486 (2001).

Macfarlane et al., "Isolating RNA from clinical samples with Catrimox-14 and lithium chloride", *J. Clin Lab Anal.*, 11, 132-139 (1997).

Washabaugh et al., "The systematic characterization by aqueous column chromatography of solutes which affect protein stability", *J Biol Chem.*, 261, 12477-12485 (1986).

(Continued)

*Primary Examiner*—Eric S Olson
(74) *Attorney, Agent, or Firm*—Seed IP Law Group PLLC

(57) ABSTRACT

Reagents, methods and kits for the purification of RNA from biological materials are provided.

46 Claims, No Drawings

OTHER PUBLICATIONS

Technical Bulletin #160: The Use of LiCl Precipitation for RNA Purification, 2003, Ambion Website @ http://www.ambion.com/techlib/tb/tb_160.html.

Ahmad, "Free Energy Changes in Ribonuclease A Denaturation," *J. Biol. Chem.*, 1983, 258(18):11143-11146.

Ahmad, "Free Energy Changes in Denaturation of Ribonuclease A by Mixed Denaturants," *J. Biol. Chem.*, 1984, 259(7):4183-4186.

Bugos et al., "RNA Isolation from Plant Tissues Recalcitrant to Extraction in Guanidine," *BioTechniques*, 1995, 19:734-737.

Chomczynski and Sacchi, "Single-Step Method of RNA Isolation by Acid Guanidinium Thiocyanate-Phenol-Chloroform Extraction," *Anal. Biochem.*, 1987, 162:156-159.

Collins, "Sticky ions in biological systems," *Proc. Natl. Acad. Sci. USA*, 1995, 92:5553-5557.

Cox and Smulian, "A single-step procedure for the isolation of individual mRNA species from crude lysates of *Physarum polycephalum*," *FEBS Letters*, 1983, 155:73-80.

Dahle and Macfarlane, "Isolation of RNA from Cells in Culture Using Catrimox-14™ Cationic Surfactant," *BioTechniques*, 1993, 15:1102-1105.

Hofmeister, "On the theory of the effects of salts," *Arch. Exp. Pathol. Pharmakol.*, 1888, 247-260.

Kazakov, "Nucleic Acid Binding and Catalysis by Metal Ions," *Bioorganic Chemistry: Nucleic Acids*, 1996, Chapter 9, pp. 244-477.

Krawetz et al., "Isolation and fractionation of total nucleic acids from tissues and cells," *J. Biochem. Biophys. Meth.*, 1986, 12:29-36.

Sambrook, "Concentrating Nucleic Acids: Precipitation with Ethanol or Isopropanol," *Molecular Cloning: A Laboratory Manual*, 1989, vol. 3, $2^{nd}$ edition, Cold Spring Harbor, pp. E10 and E15.

Witchel et al., "Milligram Quantity Preparation of RNA from a Marine Invertebrate with a High Fluid Content," *BioTechniques*, 1996, 21:1024-1026.

Wiggins, "High and Low Density Intracellular Water," *Cellular and Molecular Biology*, 2001, 47:735-744.

CRC Handbook of Chemistry and Physics, $62^{nd}$ Edition, CRC Press, Boca Raton, Florida. D-96, B-75, B-91, B-113, B-132, B-147 (1981-1982).

Jobes et al., *Taxon*, 44, 379-386 (1995).

Kondo et al., *Analytical Biochemistry*, 198, 30-35 (1991).

Lemarchand et al., *Journal of Microbiological Methods*, 63, 115-126 (2005).

Surzycki, "General Aspects of DNA Isolation and Purification", Springer-Verlag GMBH and Co. KG, Berlin, 1-32, (2000).

* cited by examiner

COMPOSITIONS AND METHODS FOR USING A SOLID SUPPORT TO PURIFY RNA

BACKGROUND OF THE INVENTION

Nucleic acids such as deoxyribonucleic acid (DNA) and ribonucleic acid (RNA) are used extensively in the field of molecular biology for research and clinical analyses. RNA may be found in nature in various forms which include messenger RNA (mRNA), transfer RNA (tRNA), ribosomal RNA (rRNA), and viral RNA each of which have distinct properties related to their specific functions. Analysis of RNA expression levels and patterns provides important information in fields such as developmental genetics, drug discovery and clinical diagnostics. For example, RNA analysis provides important diagnostic information about both normal and aberrant functioning of genes. Furthermore, gross DNA rearrangements associated with common leukemias are detected by isolation and identification of abnormal, hybrid RNAs.

Common methods for analyzing RNA include northern blotting, ribonuclease protection assays (RPAs), reverse transcriptase-polymerase chain reaction (RT-PCR), cDNA preparation for cloning, in vitro translation and microarray analyses. To obtain valid and consistent results from these analyses, it is important that the RNA be purified from other components common to biological materials such as proteins, carbohydrates, lipids and DNA.

RNA purification methods fall into two general categories, liquid phase and solid phase purification. In liquid phase purification, the RNA remains in the liquid phase while impurities are removed by processes such as precipitation and/or centrifugation. In solid phase purification, the RNA is bound to a solid support while impurities such as DNA, proteins, and phospholipids are selectively eluted. Both purification strategies utilize conventional methods, which require numerous steps and, often, hazardous reagents, as well as more rapid methods, which require fewer steps and usually less hazardous reagents. When the starting biological material comprises cells, both methods require a cell or viral co-rupture or lysis step that results in a mixture of RNA with contaminants such as DNA, lipids, carbohydrates, proteins, etc. Such mixtures also contain RNases which easily degrade RNA and must be removed and/or inactivated.

Traditionally, liquid phase RNA isolation methods have used liquid-liquid extraction (i.e, phenol-chloroform) and alcohol precipitation. Perhaps, the most commonly used liquid-liquid extraction method is the "acid-guanidinium-phenol" method of Chomczynski and Sacchi (Chomczynski P, Sacchi N., *Single-step method of RNA isolation by acid guanidinium thiocyanate-phenol-chloroform extraction*, Anal Biochem 162: 156-9 [1987]; U.S. Pat. Nos. 5,945,515, 5,346,994, and 4,843,155). This method comprises: (1) extracting the sample with a guanidinium isothiocyanate (GITC) solution to which an acidic medium, phenol, and chloroform are added consecutively; (2) centrifuging the mixture to separate the phases such that the proteins denatured by the phenol may be removed from the nucleic acids which are found in an intermediate layer; (3) adding an alcohol so as to precipitate and thereby concentrate the RNA; and (4) washing and re-hydrating the purified RNA. Although this method ensures the purification of RNA, it utilizes hazardous reagents such as chloroform and phenol. Precipitation of nucleic acids by cationic detergents is another example of liquid phase technology (U.S. Pat. Nos. 5,985,572, 5,728,822, and 5,010,183 (MacFarlane)). For example, U.S. Pat. No. 5,985,572 discloses a novel method for isolating RNA from biological samples using selected quaternary amine surfactants. A non-hazardous liquid phase purification method was disclosed by Heath (U.S. Pat. No. 5,973,137) using low pH lysing and precipitation reagents. However, liquid phase methods have serious disadvantages in that they involve tedious precipitation steps, and are consequently difficult to automate. Thus, the need for high-throughput RNA purification has led to the development of solid phase methods. As with liquid phase purification, conventional solid phase methods have been developed to generate highly purified RNA. Generally, these methods require four general steps: lysing cells or viral coats to release RNA; binding the released RNA to a solid support; washing away impurities; and then eluting the purified RNA. The first two steps, lysing the cells or viral coats and binding the released RNA, have traditionally required hazardous reagents.

Solid phase methods can be classified broadly according to the type of solid phase used for such extractions, either silica or ion-exchange resins. For solid phase nucleic acid isolation methods, many solid supports have been used including membrane filters, magnetic beads, metal oxides, and latex particles. Probably the most widely used solid supports are silica-based particles (see, e.g., U.S. Pat. No. 5,234,809 (Boom et al.); International Publication No. WO 95/01359 (Colpan et al.); U.S. Pat. No. 5,405,951 (Woodard); International Publication No. WO 95/02049 (Jones); WO 92/07863 (Qiagen GmbH). Nucleic acids bind to silica in the presence of chaotropic agents. For example, the method disclosed in U.S. Pat. No. 5,234,809 (Boom et al.) uses a high concentration chaotropic solution such as guanidine thiocyanate to bind DNA to silica particles and requires six centrifugation steps and five reagents to purify DNA from whole blood.

Specifically, Boom teaches (1) mixing the biological material with a solution consisting of guanidine thiocyanate, EDTA and Triton X-100, and silica; (2) allowing the nucleic acid to bind to the silica; (3) washing the silica with consecutive washes of guanidine thiocyanate, ethanol, acetone; and (4) eluting the nucleic acid with an eluent. Disadvantages of this method are the use of a particulate suspension, the use of many centrifugation steps, and the use of hazardous reagents, such as guanidine isothiocyanate and acetone. However, although this method has been employed successfully for DNA isolation, it is unsuitable for RNA isolation due to unacceptable levels of DNA contamination.

The prior art also teaches the use of ion-exchange resins to which nucleic acids bind at low pH and from which they are eluted at a higher pH (and/or higher salt concentration). See U.S. Pat. No. 5,057,426 (Henco et al.). However, such methods are primarily advantageous for the selective separation of long-chain nucleic acids which have a distinctive charge from smaller nucleic acids and other biological materials such as proteins. Such methods would not be successful for the isolation of RNA, irrespective of length and charge, from the remainder of the biological material.

Furthermore, the long-chain nucleic acids must be eluted at high salt concentrations for an ion-exchange method to work. Commonly used salts (e.g., NaCl and KCl) can interfere with many enzymes used in molecular biology. Thus, for many applications, ion-exchange isolation of nucleic acids requires a final desalting step.

Polycationic solid supports have also been used in the purification of nucleic acids from solutions containing contaminants. See U.S. Pat. No. 5,599,667 (Arnold et al.) Polycationic supports selectively adsorb nucleotide multimers based on their size, the larger multimers having a higher affinity for the polycationic support than the smaller ones. This method is based largely on the affinity between positively charged cationic solid supports and negatively charged phosphate backbones of nucleotides. Larger nucleotide multimers have higher charges and will consequently bind preferentially over smaller nucleotide multimers. Thus, the method of Arnold is suited to the isolation of nucleotide multimers based on size rather than the isolation of all types of RNA from crude biological materials. Furthermore, the method of Arnold limits itself to the use of polycationic supports composed of cations such as ammonium, immonium and guanidinium ions.

A recent purification method employs the principle that RNA precipitates preferentially in the presence of guanidinium salts under defined buffer conditions. See U.S. Pat. No. 5,972,613 (Somack et al.). In this method, RNA is precipitated in the presence of guanidinium salts at low temperatures, while the DNA remains in solution. Yet another method employs this principle, with the added presence of lithium salts. See U.S. Pat. No. 5,990,302 (Kuroita et al.). In this method, the biological material is lysed in an acidic solution containing a lithium salt and a chaotropic agent such as guanidinium isothiocyanate (GITC), after which the RNA is brought into contact with a nucleic acid-binding carrier such as silica. The RNA is subsequently purified by eluting from the silica in a low ionic-strength buffer. However, this method is disadvantageous in its use of hazardous substances such as the chaotropic salt, guanidine thiocyanate.

Combinations of chaotropic substances such as guanidine thiocyanate, guanidine hydrochloride, sodium iodide, and lithium chloride/urea mixtures at ionic strengths greater than 4 M in conjunction with silica-based carriers have been taught by Hillebrand et al. See WO 95/34569. However, this invention is limited to a one-step method involving a slurry of silica beads to which the aforementioned chaotropic substances are added.

Thus, to advance the field of RNA purification there is a need for solid phase RNA purification strategies. There is also a need for reagents and methods that are adaptable to solid phase purification strategies which are not only simple and rapid, but general in scope to maximize adaptability for automation. There is a need for reagents that are stable at room temperature (i.e., 20-25° C.), less hazardous (i.e., less corrosive or toxic), nonparticulate to eliminate the need for mixing, and protective of RNA quality. There is also a need for methods with few steps that can be performed using a variety of biological starting materials, whether hydrated or dried, especially as applied to routine testing as found in clinical and research laboratories. In addition the RNA purification reagents must not inhibit subsequent RNA analysis procedures by carrying over particulates or interfering with the buffering capacity or ionic conditions of downstream analyses such as: reverse transcriptase reactions, amplification reactions, nuclease protection assays, northern blotting, and microarray and other labeling reactions.

SUMMARY OF THE INVENTION

The present invention provides reagents, methods, and kits that incorporate a solid support for isolating substantially pure and undegraded RNA from liquid and dried biological samples The purified RNA is suitable for use in widely used analytical and diagnostic methods such as RT-PCR and microarray analyses that require substantially pure and undegraded RNA.

The present invention consists of a combination of unique reagents that may be used to purify RNA from a variety of biological materials without the use of hazardous substances such as phenol, and chloroform, or hazardous chaotropic substances such as guanidinium salts, urea, etc. Furthermore, the reagents and methods taught in the present invention allow for the elution of RNA in low salt reagents thus eliminating tedious desalting steps found in the prior art. The reagents taught by the invention include a unique neutral to high pH RNA Binding Solution, an RNA wash solution, and an RNA elution solution. When the biological material is comprised of cellular or viral material, the RNA Binding Solution comprises a detergent to make it an RNA Lysing Solution as well. These reagents used in conjunction with an appropriate solid support to purify substantially pure and undegraded RNA which is substantially pure and contaminant-free.

The present invention teaches the use of a unique neutral to high pH RNA Binding Solution Binding Solution. This RNA Binding Solution allows nucleic acids to preferentially bind to a solid support of choice because of the presence of an RNA-complexing salt, preferably an alkali-metal salt in a buffer. In one embodiment, the RNA Binding Solution additionally comprises an amphiphillic reagent, such as a detergent, that gives it cell lysing capabilities. This RNA Binding Solution may be referred to as an RNA Lysing Solution. The RNA Lysing Solution lyses the biological material while conferring unique binding properties to the nucleic acids released following lysis such that they preferentially bind to a solid support of choice over other contaminants such as proteins, phospholipids, etc. The RNA Lysing Solution of the present invention achieves this preferential binding by the presence of an RNA-complexing salt such as an alkali-metal salt in a buffer, and optionally an amphiphillic reagent, without the use of hazardous chaotropic substances such as guanidinium salts, urea, etc. The RNA-complexing salt is called as such because it complexes with the charged phosphate backbone of nucleic acids such as RNA. The amphiphillic reagent in the RNA Lysing Solution is preferably a detergent that aids in lysing the biological material. Although, all types of detergents may be used to practice the invention, non-ionic detergents are preferred because they are more soluble in high concentration salt solutions.

The RNA Binding Solution and RNA Lysing Solution are buffered to maintain the pH at least about 7 (preferably, at least about 8, more preferably, at least about 8.5, and most preferably, at least about 9). A neutral to basic pH enhances the ability of the nucleic acids, particularly RNA, to bind to the solid support. It is also observed that binding of nucleic acids in the presence of low pH reagents is significantly inhibited. The RNA Binding Solution and RNA Lysing Solution comprise a buffer to adjust the pH as desired. The buffer preferably has a pKa of at least about 8. A preferred buffer is tris(hydroxymethyl)aminomethane (Tris)

Suitable RNA-complexing salts include alkali-metal salts such as sodium, potassium, lithium, cesium, and rubidium salts. A preferred alkali-metal salt is a lithium salt. Lithium salts used to practice the present invention include, but are not limited to, lithium chloride, and lithium bromide. Preferential binding of RNA to a solid support is enhanced by high concentrations of alkali-metal salts. Preferably, the alkali-metal salt is at a concentration of between 4-10 M. The RNA Lysing Solution additionally comprises an amphiphillic reagent. In one embodiment, the amphiphillic reagent is a detergent. The detergent may be anionic, cationic, zwitterionic or nonionic but is preferably non-ionic. Examples of non-ionic detergents include detergents from the Tween, Triton, Tergitol and Nonidet classes of detergents. Preferably, the detergents are present at a high concentration of about 10%. The combination of an alkali-metal salt and a detergent, each at the aforementioned high concentrations in a neutral to high pH buffer also serves to neutralize the harmful effects of enzymes such as RNases, generally associated with biological material. Optionally, the RNA Binding Solution and RNA Lysing Solution may also contain a chelating agent.

The invention also incorporates the use of an RNA wash solution to remove impurities such as proteins and phospholipids from the solid support while allowing the nucleic acids to remain bound to the solid support. The RNA wash solution comprises a high concentration of alcohol, and a suitable salt buffered at a neutral pH of between 6-8 M to remove contaminants such as protein, lipids, etc.

The simplicity and efficiency of the RNA Binding Solution (or RNA Lysing Solution), and RNA wash solution in conjunction with an appropriate solid support results in the use of a simple RNA eluting solution such as RNase-free water, or alternately RNase-free water with a non-ionic detergent to elute the RNA from the solid support. Thus, the problems of desalting of RNA commonly encountered in the high salt wash solutions of the prior art are avoided.

The present invention also teaches methods for the isolation of RNA from biological material. The biological material includes, for example, cell or viral suspensions, body fluids and wastes, whole blood, bone marrow, buffy coat, plasma, cultured cells, all suspensions (e.g., bacteria, tissue homogenates), crude or partially purified mixtures of nucleic acids, and environmental samples. The environmental samples include, for example, air, water or soil.

The versatility and effectiveness of the RNA Binding Solution or RNA Lysing Solution lends itself to two viable alternative methods for RNA isolation. In the first method, the biological material is contacted with the RNA Binding Solution or RNA Lysing Solution before it is contacted with the solid support. In one embodiment, when the biological material comprises cellular or viral material, the RNA Lysing Solution is preferentially used. This method serves to lyse the cells and release the nucleic acids including RNA. In the second method, the RNA Binding Solution or RNA Lysing Solution is added directly to the solid support and allowed to bind to the solid support, thereby eliminating a step, and further simplifying the method. In this latter method, the RNA Binding Solution or RNA Lysing Solution is directly applied to the solid support and then dried on the solid support before contacting the biological material with the treated solid support.

Suitable solid supports include cellulose, cellulose acetate, nitrocellulose, nylon, polyester, polyethersulfone, polyolefin, polyvinylidene fluoride, and combinations thereof. The solid support may be encased or immobilized in a vessel to enable plug-flow or continuous-flow RNA isolation methods. Alternately, the material of the solid support may be packed so as to create a free-standing solid support such as a membrane, disk, or cylinder that may be immobilized or encased in a suitable vessel. In one embodiment, the solid support may be fibrous or particulate to allow optimal contact with the biological material.

The present invention also provides kits for purifying RNA comprising instruction means for preparing substantially pure and undegraded RNA from a biological sample and one or all of the following: RNA Binding Solution or RNA Lysing Solution, a solid support either untreated or treated with an RNA Binding Solution or RNA Lysing Solution, an RNA wash solution, an RNA eluting solution or any combination thereof. In addition, the kit can include a vessel to contain the solid support, vessels to contain substantially pure and undegraded RNA, and combinations thereof. Substantially pure, undegraded RNA is RNA that is suitable for use in subsequent analyses known to those with skill in the art, for example, RT-PCR, in vitro translation, northern blotting, microarray analysis etc.

DETAILED DESCRIPTION OF THE INVENTION

The present invention provides reagents, methods and kits for purifying RNA from biological samples. Such biological samples include biological material, typically in an aqueous mixture or dried, that contains RNA, including complex biological mixtures of prokaryotic or eukaryotic cells. Preferably, the methods and kits of the present invention isolate a wide range of RNAs. Candidate RNAs include, but are not limited to, ribosomal RNA, messenger RNA, transfer RNA, and viral RNA, or combinations thereof, all of which can be recovered over a wide molecular weight range. Typically, the biological material also contains DNA, carbohydrates, proteins, and lipids. Biological materials include, but are not restricted to the following: body fluids such as whole blood, bone marrow, blood spots, blood serum, blood plasma, buffy coat preparations, saliva and cerebrospinal fluid, buccal swabs, cultured cells, cell suspensions of bacteria or tissue homogenates, solid animal tissues such as heart, liver and brain, body waste products, such as feces and urine, environmental samples taken from air, water, sediment or soil, plant tissues, yeasts, bacteria, viruses, mycoplasmas, fungi, protozoa, rickettsia, and other small microbial cells. Lysates, homogenates, or partially purified samples of these biological materials may also be used. In one embodiment, the biological material comprises crude or partially purified mixtures of nucleic acids.

The reagents, methods and kits of the present invention provide substantially pure and undegraded RNA with relatively little contaminating genomic DNA or other impurities such that the RNA may be used in downstream processes such as RT-PCR and microarray analyses. As used herein, "substantially pure" means substantially free of genomic DNA, carbohydrate, protein, lipid impurities, such that the RNA can be used in subsequent analyses known to those with skill in the art such as RT-PCR and microarray analyses. As used herein, "substantially undegraded" RNA means nondigested or intact RNA, which can be readily determined by one of skill in the art using standard techniques. That is, the RNA is not damaged by enzymatic, physical or chemical means during the purification methods of the present invention.

The reagents, methods and kits of the present invention may be used to purify substantially pure and undegraded RNA over a wide range of biological sources, and life forms, all of which can be recovered over a wide molecular weight range. The substantially pure and undegraded RNA obtained from practicing the invention can also be evaluated for purity, yield, size, reverse transcriptase or other hybridization processes, amplification, hybridization ability, etc. The substantially pure and undegraded RNA is representative of the total RNA found in the biological sample, and is typically a combination of, but not restricted to, mRNA, tRNA, rRNA, and viral RNA.

The biological samples include, for example, cell or viral suspensions and pellets thereof, body fluids, and tissue homogenates, etc. If the biological sample consists of cells or viruses, the cells or viruses may be enumerated prior to this step. The enumeration may be conducted using standard cell counting methods such as an electronic cell counter (e.g., CBC5 Coulter Counter, Coulter Corp., Hialeah, Fla.) or a visual counting chamber (e.g., a hemacytometer, Bright Line, American Optical, Buffalo, N.Y.).

1. Reagents: The present invention comprises three categories of reagents. These are respectively the RNA Binding Solution (alternatively referred to as the RNA Lysing Solution when it additionally comprises an amphiphillic reagent), the RNA wash solution, and the RNA elution solution.

(i) RNA Binding Solution and RNA Lysing Solution: The RNA Binding Solution allows nucleic acids to preferentially bind to the solid support of choice. The RNA Lysing Solution enables efficient lysis of the biological sample to release the nucleic acids, and allows them to preferentially bind to the solid support of choice. The RNA Binding Solution comprises the following components: a buffer; an alkali-metal salt; and optionally a chelating agent. The RNA Lysing Solution is comprised of the same elements as the RNA Binding Solution, but additionally comprises an amphiphillic reagent, such as a detergent. The RNA Binding Solution and RNA Lysing Solution are unique in that they require no added strong chaotropic substances such as guanidinium salts, urea, etc. Guanidinium salts and urea are strong chaotropic salts that disrupt the structure of water and thus tend to decrease the strength of hydrophobic interactions resulting in a drastic effect on other solute molecules. For example, urea, when dissolved in water, disrupts the secondary, tertiary, and quaternary structures of proteins, and subsequently causes dissociation of proteins from RNA. Guanidinium salts and urea dissolve in water through endothermic reactions. Both guanidinium salts and urea are considered to be strongly chaotropic salts as defined by the Hofmeister series, a widely used system that ranks cations and anions according to relative chaotropic strength (F. Hofmeister, *On the understanding of the effects of salts*, Arch. Exp. Pathol. Pharmakol. (Leipzig) 24 (1888) 247-260).

In comparison, neither lithium cation (Li+) nor chloride anion (Cl−) are strongly chaotropic in the Hofmeister Series. Under this scheme, for example, chloride anion is generally considered a kosmotrope, and lithium cation exhibits similar solvent effects as sodium cation; hence, LiCl is not a strong chaotrope, and may be considered a kosmotrope. High-concentration Li salts, such as LiCl, expose only one of three tryptophanyl residues in RNase A as compared with all three tryptophanyl groups with guanidinium hydrochloride or urea (Ahmad F., J Biol Chem Sep. 25, 1983; 258 (18):11143-6, *Free energy changes in ribonuclease A denaturation: Effect of urea, guanidine hydrochloride, and Lithium Salt*.). These results indicate that LiCl induces only local perturbations in protein structure without global effects on secondary, tertiary, or quaternary structure. Thus, LiCl is not a chaotrope with broad-range utility for protein unfolding. In contrast, guanidinium salts are effective at unfolding virtually all proteins. Furthermore, unlike strong chaotropic salts, the reaction of lithium salts such as lithium chloride in water is an exothermic reaction. Differences such as these are indicative of the differences between strong chaotropic substances, such as guanidinium salts, and the alkali-metal salts of the present invention and affect their interaction with other components of the RNA Binding Solution and RNA Lysing Solution which consequently affect RNA binding to the solid support.

The first component of the RNA Binding Solution or RNA Lysing Solution is a buffer that maintains the pH of said solutions to at least about 7, preferably, at least about 8, more preferably, at least about 8.5, and most preferably, at least about 9. The buffer preferably has a pKa of at least about 8, and is preferably used at a concentration of 10-100 mM. A preferred buffer is Tris buffer. Optionally, a base may be used to adjust the pH of the RNA Binding Solution or RNA Lysing Solution. Preferably, the base is one that can raise the pH of said solutions to no less than 7. The base is preferably an alkali-metal hydroxide. Such alkali-metal hydroxides include sodium hydroxide, potassium hydroxide, and lithium hydroxide. The neutral to high pH of the RNA Binding Solution or RNA Lysing Solution enhances the ability of nucleic acids, particularly RNA, to bind to the solid support.

The second component of the RNA Binding Solution or RNA Lysing Solution is an RNA-complexing salt that confers unique binding properties to nucleic acids, such as RNA, such that the nucleic acids can preferentially bind to the solid support over other contaminants such as proteins, phospholipids, etc. Preferably, such an RNA-complexing salt is an alkali-metal salt. Suitable salts include sodium, potassium, and lithium salts. Preferably, the salts are sodium chloride, potassium chloride, and lithium chloride. Most preferably, the salt is lithium chloride. Preferably, the salt is present at a high salt concentration of between 4-10 M.

The RNA Lysing Solution additionally comprises an amphiphillic reagent. This reagent is comprised of a compound or molecule having a hydrophilic group attached to a hydrophobic functionality such as a hydrocarbon chain and having surfactant properties. In one embodiment, the amphiphillic reagent is a detergent. Although, anionic, cationic, and zwitterionic detergents may all be used, RNA isolation is optimally achieved through the use of a non-ionic detergent. Non-ionic detergents lack polar groups and are the mildest of all detergents. Although, any nonionic detergent may be used, the non-ionic detergents are preferably those from the Tween class (Tween-20, Tween-40, Tween-60, Tween-80, etc.), the Triton class (X-100, X-114, XL-80N, etc), Tergitols (XD, TMN-6, etc.) and Noniodets (NP-10, NP-40, etc). Preferably, the nonionic detergent is used at a concentration of 2-20%, more preferably at about 10%. Combinations of non-ionic detergents may also be used. For example, a Tween and a Triton may be used in various ratios, for example, a 1:1 ratio.

In order to prevent degradation of the RNA, RNase-free water is used in the RNA Binding Solution or RNA Lysing Solution. Optionally, a chelating agent may also be used in either solution to prevent degradation of contaminating DNA. The use of a chelating agent prevents DNA polymers from being degraded to smaller fragments which may cause additional contamination problems. Preferably, the chelating agent is present at a concentration of 1-100 mM; more preferably, the chelating agent is present at a concentration of 1-10 mM. Preferably, the chelating agent is EDTA or CDTA.

The RNA Binding Solution and RNA Lysing Solution possess significant advantages over reagents used in the prior art. In the case of the RNA Lysing Solution, the unique combination of an RNA-complexing salt, and detergent as taught by the present invention, each at the aforementioned high concentrations in a neutral to high pH buffer help inactivate enzymes harmful to RNA, such as RNases, without the use of such reagents as phenol, chloroform, and guanidinium salts. Additionally, both RNA Binding Solution and RNA Lysing Solution confer a high binding property to the nucleic acids such that they tightly bind with the solid support of choice.

(ii) RNA Wash solution: The present invention also teaches an RNA wash solution having a low salt concentration. The RNA Wash solution is used to wash the solid support to which nucleic acids are bound so as to rid it of non-nucleic acid contaminants such as proteins, phospholipids, etc. The RNA wash solution comprises an alcohol preferably at a concentration greater than 50%; a buffer, and a salt at a low concentration. Optionally, the RNA wash solution comprises a chelating agent. For the purposes of the present invention, the low salt concentration means a salt concentration for which downstream desalting steps are unnecessary to prevent the inhibition of downstream processing methods such as RT-PCR. A preferred RNA wash solution is Gentra RNA wash solution (Part. No. S2-0025, Gentra Systems, Inc., Minneapolis, Minn.).

(iii) RNA elution solution: RNA bound to the solid support may be preferentially eluted using n RNA elution solution while leaving the contaminating DNA bound to the solid support. The simplicity of the reagents used in lysing the biological material and binding of the RNA to the solid support, and in washing the solid support taught by the present invention lends itself to a simple RNA elution solution. In one embodiment, RNAse-free water, preferably treated with a substance that inactivates RNases such as diethyl pyrocarbonate (DEPC) may be used. Other RNA elution solutions known to those skilled in the art may also be used. A preferred RNA elution solution is Gentra RNA elution solution (Part. No. S3-0025 Gentra Systems, Inc., Minneapolis, Minn.).

2. Solid Support: A variety of solid supports may be used in the present invention. These include solid supports made of cellulose, cellulose acetate, nitrocellulose, nylon, polyester, polyethersulfone, polyolefin, polyvinylidene fluoride, and combinations thereof. The size of the solid support suitable for use with the reagents of this invention may vary according to the volume of biological material. For example, when Schleicher and Schuell 903 paper, which has a thickness of 0.5 mm, is used for the solid support, a 3 mm diameter disk will hold about 3 µl biological material, whereas an 8 mm diameter disk will hold about 25 µl biological material. As the volume of the biological material increases, the thickness and/or diameter of the solid support may increase accordingly.

Preferably, the solid support will be a material that permits the preferential binding of nucleic acids to the solid support in the presence of the aforementioned RNA Lysis Reagent over other biological contaminants. Preferably, such a solid support is comprised of bonded polyester fibers, for example, Filtrona® Filter Media (Lot. No. R-20653). In one embodiment, the polyester fibers are fragmented to create smaller particles so as to be accommodated in alternate vessel configurations, or shaped in alternate configurations. One configuration may be an independent free-standing solid support.

The shape of the solid support suitable for use with the reagents of this invention may be, for example, a sheet, a precut disk, cylinder, single fiber, or a solid support composed of particulates. The material of the solid support may be packed so as to create a free-standing solid support such as a membrane, disk, or cylinder that may be immobilized or encased in a suitable vessel. If necessary, the solid support is contained in an appropriate vessel, e.g., a paper form (such as a Guthrie card), a microcentrifuge tube, a spin tube, a 96-well plate, a chamber, or a cartridge. If the solid support comprises fibers, it may be encased in a suitable vessel so as to pack the fibers appropriately, allow for optimal nucleic acid binding, and the washing away of contaminants such as protein, phospholipids, etc.

In one embodiment, the solid support may be pre-treated with the RNA Binding Solution or RNA Lysing Solution to reduce the number of steps for RNA isolation. The RNA Lysing Solution is used when the biological material comprises cellular or viral material so as to lyse the biological material and bind the nucleic acids in a single step. Preferably, the volume of the RNA Binding Solution or RNA Lysing Solution used to treat the solid support is at least one-tenth of the total volume of the solid support. More preferably, the volume of the RNA Binding Solution or RNA Lysing Solution is at least half the total volume of the solid support, and most preferably, the volume of the RNA Binding Solution or RNA Lysing Solution corresponds to the total volume of the solid support. The total volume of the solid support refers to the volume defined by the external boundaries of the solid support. The external boundaries may be dictated by the shape and/or internal boundaries of the vessel containing the solid support. The RNA Lysing Solution may be bound covalently, non-covalently, by being trapped within the interstitial spaces of the solid support, or by being deposited on the material (e.g., fibers, beads, etc.) of the solid support. Preferably, the RNA Binding Solution or RNA Lysing Solution is allowed to dry on the solid support.

In another embodiment of the invention, the RNA Binding Solution or RNA Lysing Solution may be added directly to the material (e.g., fibers, etc.) used in making the solid support and preferably allowed to dry before it is made into the final user-ready form (e.g., paper, swab, disk, plug, column, etc.).

In order that the invention may be better understood, specific embodiments for vessels that contain the solid support will now be described in more detail.

In one preferred embodiment of this invention, the vessel is a cartridge equipped with one or more inlet ports or pierceable septa at the top. The inlet ports are attached to vessels upstream containing the sample or reagents through a connector, such as a female Luer-Lock. One inlet, the sample port, is used for the application of the biological sample to the solid support. An optional feature on the sample port is a self-sealing mechanism that seals the sample port after sample has been transferred through it. The second inlet serves as a reagent port. An optional feature on both inlet ports is a protective breakaway seal. Furthermore, the inlet ports, breakaway seals and diffuser may be housed in an optional screw-cap. At the bottom of the solid support is an optional diffuser with a pore size suitable for the dispersion and passage of cellular debris, proteins and lipid molecules. The diffusers allow for a uniform traversal of biological material across the cross section of the cartridge, and prevent unequal buildup of biological material anywhere above or below the solid support. The outlet of the cartridge comes equipped with a protective cap that fits neatly over the tapered barrel. The purified RNA is collected in a collection tube that consists of a conical tube with a snap cap for easy and contamination-free storage. The entire vessel can be scaled in size depending on the size of the samples to be processed and the yields needed for subsequent analysis. For instance, a preferred solid support fashioned out of a Filtrona® Filter Media (Lot. No. R-20653) filter with dimensions of 25.2 mm (circumference) by 3 to 10 mm length which is encased in a suitable tube may either be scaled in size and placed in a larger tube to process larger samples, or alternatively, such filters may be stacked on top or below each other in a tube in order to accommodate varying sample volumes and achieve similar results.

In another preferred embodiment of this invention, the vessel consists of a spin tube designed to hold an insert into which the solid support is packed. The solid support may be cellulose, cellulose acetate, nitrocellulose, nylon, polyester, polyethersulfone, polyolefin, polyvinylidene fluoride, and combinations thereof. The insert consists of a flanged top to hold it in the spin tube and a perforated bottom to allow fluids to pass through while supporting the solid support. A cap tethered to the spin tube may be used to cover the insert. Solutions, for instance, RNA Lysing solution containing non-nucleic acid contaminants, RNA wash solution, or RNA elution solution containing RNA, pass through the perforated bottom and are collected at the bottom of the spin tube by centrifugal forces that draw out the aforementioned solutions.

In yet another embodiment, the vessel may be multiple well plates, for example, 6, 12, 24, 48, 96, or 384 well plates where a solid support is packed into each well. The bottom of each well has an exit port through which solutions containing contaminants or purified RNA can pass.

The unique combination of the solid support of choice with the unique reagents—RNA Binding Solution (or RNA Lysing Solution), RNA wash solution, and RNA elution solution—results in the isolation of substantially pure, undegraded RNA. The properties of the RNA Binding Solution or RNA Lysing Solution as described above permit preferential binding of the nucleic acids to the solid support, while the RNA Elution solution permits the preferential elution of the RNA from the solid support over that of DNA.

3. Methods: The present invention also provides methods for purifying RNA from biological material. The reagents and solid supports taught in the invention lend themselves to two alternate isolation methods. In the first method, the biological material is contacted with the RNA Binding Solution or RNA Lysing Solution before it is contacted with the solid support. When the biological material comprises cellular or viral material, the RNA Lysing Solution is used to lyse the biological material and release the RNA before adding it to the solid support. Additionally, the RNA Lysing Solution prevents the deleterious effects of harmful enzymes such as RNases. The RNA Lysis solution may be successfully used to lyse cultured cells or white blood cells in pellets, or to lyse cells adhering to or collected in culture plates, such as standard 96-well plates. If the biological material is composed of tissue chunks or small particles, the RNA Lysis solution may be effectively used to grind such tissue chunks into a slurry because of its effective lysing capabilities. The RNA Lysis solution volume may be scaled up or down depending on the cell numbers or tissue size. Once the biological material is lysed, the lysate may be added directly to the solid support to incubate for at least one minute to allow binding of nucleic acid to the solid support. Preferably, the lysate is allowed to incubate for at least 5 minutes. In another embodiment, when the biological material is composed of a crude or partially purified mixture of nucleic acids, the RNA Lysing Solution of the present invention may be used to dissociate proteins from the RNA.

In the second method, the RNA Binding Solution or RNA Lysing Solution may be added directly to the solid support, thereby eliminating a step, and further simplifying the method. In this latter method, the RNA Binding Solution or RNA Lysing Solution may be applied to the solid support and then dried on the solid support before contacting the biological material with the treated solid support. For example, in one embodiment, a suitable volume of RNA Lysing Solution or RNA Binding Solution is directly added to a solid support placed in a Spin-X basket which is further placed in a 2 ml spin tube. The solid support is heated until dry for at least 12 hours at a temperature of between 40-80° C., after which any excess unbound RNA Lysing Solution or RNA Binding Solution is removed, and is then stored under dessication. The biological material may be directly added to the solid support pre-treated with the RNA Lysing Solution or RNA Binding Solution, and allowed to incubate for at least one minute, preferably at least 5 minutes, until it is suitably lysed and the nucleic acids are released, and bound to the solid support.

When the biological materials comprise cellular or viral materials, direct contact with the RNA Lysing Solution, or contact with the solid support pre-treated with the RNA Lysing Solution causes the cell and nuclear membranes, or viral coats, to solubilize and/or rupture, thereby releasing the nucleic acids as well as other contaminating substances such as proteins, phospholipids, etc. The released nucleic acids, selectively bind to the solid support in the presence of the RNA-complexing salt.

After, this incubation period, the remainder of the biological material is optionally removed by suitable means such as centrifugation, pipetting, pressure, vacuum, or by the combined use of the aforementioned means with an RNA wash solution such that the nucleic acids are left bound to the solid support. Preferably, the remainder of the non-nucleic acid biological material which includes proteins, phospholipids, etc., are removed first by centrifugation, such that the unbound contaminants in the lysate are separated from the solid support. This is followed by one or more wash steps using an adequate volume of a suitable RNA wash solution. Each wash step is followed by a centrifugation step. Preferably, the number of wash steps is at least two, more preferably the number of wash steps is at least three. The multiple wash steps rid the solid support of substantially all contaminants, and leave behind nucleic acids preferentially bound to the solid support.

Subsequently, the bound RNA is preferentially eluted using an adequate amount of an RNA elution solution known to those skilled in the art, leaving the contaminating DNA bound to the solid support. Preferably, the solid support is then centrifuged, or subject to pressure or vacuum, to release the RNA from the solid support and is collected in a suitable vessel.

As another aspect of this invention, a kit is provided that includes specific protocols, which in combination with the reagents and optionally the solid supports described herein, may be used for purifying RNA from biological materials according to the methods of the invention. The kit includes instruction means.

This invention will be further described by reference to the following detailed examples. These examples are offered to further illustrate the various specific and illustrative embodiments and techniques. It should be understood, however, that many variations and modifications may be made while remaining within the scope of the present invention.

All of the raw materials mentioned below are readily available from commercial sources such as Sigma Chemical Company, St. Louis, Mo. All percentages are in volume per volume, based on the total volume of the reagent, unless specified otherwise.

Example 1

Isolation of RNA from Human Cultured Cells

Cultured K562 cells, a human lymphoblastoid cell line, were obtained from ATCC (Manassas, Va.) and cultured using ATCC recommended medium. The cells were counted using a hemacytometer and sample volumes containing 2 million cells were distributed to 1.7 ml microfuge tubes. The cells were pelleted and centrifuged for 20 seconds at 12000 g, the supernatant fluid removed. These cell pellets were then frozen at −80° C. until use.

The cultured cells were thawed on ice and RNA was purified from the cells by adding 200 µl RNA Lysis Solution (5% Triton X-100, 5% Tween 20, 7.2 M Lithium Chloride, 10 mM EDTA, in 50 mM Tris buffer, pH 8.8) and pipetting up and down gently to adequately lyse the cells. The resulting lysate was then added to a solid support (Filtrona® Filter Media Lot No. R-20653, Filtrona Richmond, Inc. (Richmond, Va.)) of approximate dimensions of 8 mm diameter and 5 mm length positioned in the insert of a 2 ml microfuge tube (Spin-X, Catalog No. 9424, Corning Costar, Cambridge, Mass.). The lysate was incubated with the solid support for 5 minutes to allow the nucleic acids released from the lysed cells to preferentially attach to the solid support. The microfuge tube containing the solid support and biological material was centrifuged for 10 seconds at 12,000×g to collect the excess lysis solution, including contaminants such as proteins, phospholipids, etc., leaving the nucleic acids attached to the solid support. Subsequently, a volume of 200 µl RNA Wash solution (Gentra RNA wash solution (Part. No. S2-0025, Gentra Systems, Inc., Minneapolis, Minn.)) was added to the solid support and centrifuged for 10 seconds at 12,000×g. The insert containing the solid support was then transferred to a second 2 ml waste collection tube. This wash step was repeated for a total of three consecutive wash steps. However, the third wash was followed by centrifugation for 20 seconds instead of 10 seconds.

The insert containing the solid support was then transferred to a clean 2 ml collection tube. To release the RNA from the solid support, a volume of 100 µl RNA elution solution (Part. No. S3-0025, Gentra RNA elution solution, Gentra Systems, Minneapolis, Minn.) was added and allowed to incubate at room temperature for 5 minutes. The collection tube was centrifuged for 60 seconds at 12,000×g to collect the purified RNA into a 2 ml collection tube. The purified RNA was then stored on ice until ready for use. Samples that were not used immediately were stored adequately at −70° C. to −80° C.

Example 2

Evaluation of Detergents for RNA Purification

Different detergents were added to a buffered solution consisting of 7.2 M LiCl and evaluated for the ability to determine the best type of detergent needed to optimize RNA yields. The following detergents were tested: 1% ammonium lauryl sulfate, 1% dodecyl-trimethylammonium bromide (CTAB), 10% Tween-20 and 10% Triton X-100. The detergents were added to a buffer consisting of 45 mM Tris, pH 8.8. A 200 µl volume of each mixture was added to a solid support (Filtrona® Filter Media Lot #. R-20619, Filtrona Richmond, Inc. (Richmond, Va.)) and dried for 19 hours at 60° C. Two million K-562 cells were suspended in phosphate buffered saline (PBS) containing 10 mM EDTA and pipetted onto the solid support. RNA was purified by washing the solid support three times with 200 µl RNA wash solution (Gentra RNA wash solution (Part. No. S2-0025, Gentra Systems, Inc., Minneapolis, Minn.)) and eluted with 100 µl RNA elution solution. In this case, RNase-free water was used as the RNA elution solution. To determine the yield of RNA, a 1:20 dilution of each sample was prepared in deionized water. A buffered solution such as TE (10 mM Tris, 1 mM EDTA, pH 8.0) may also be used as a diluent. Absorbences at 320 nm (background), 260 nm, and 280 nm were read using a Beckman DU64 Spectrophotometer (Beckman Instruments, Inc., Fullerton, Calif.), standardized against a blank containing RNA elution solution. The RNA concentration was calculated as follows: $(A_{260}-A_{320}) \times 40$ µg/ml (RNA Extinction Coefficient)×50 (Dilution Factor); the RNA yield was calculated by multiplying the RNA concentration by the recovered elution volume. An estimate of RNA purity is the absorbance ratio at 260 nm and 280 nm, $A_{260}/A_{280}$. If the value of this ratio is between 1.8 and 2.1, the sample is considered relatively free of proteins and other contaminants. This ratio is calculated as follows: $(A_{260}-A_{320})/(A_{280}-A_{320})$. Both semi-quantitative and qualitative assessments were made by 2% agarose gel electrophoreses. The quantity of RNA was estimated by examining the intensity of ethidium bromide staining. The quality of RNA was assessed by the presence of ribosomal bands with the 28s fragment roughly twice the intensity of the 18s band. A further indication of quality was the reduction or absence of genomic DNA which was present as a much higher molecular weight band than the RNA bands.

Thus, a volume of 5 µl sample of each RNA sample was mixed with a 10× tracking dye and loaded into a 2% agarose gel. The RNA was size separated by electrophoresis at 100 volts for 30 minutes with 0.125 µg per ml ethidium bromide in both gel and running buffer to allow visualization. Following electrophoresis, the fluorescent RNA bands were visualized on a transilluminator with a Kodak Digital Imaging System EDAS 120 LE (Kodak, Rochester, N.Y.).

All three types of detergents were effective as additives in the RNA Lysis Solution in purifying RNA, giving RNA yields between 4.9 µg and 6.2 µg. This was confirmed by relative equivalence of RNA staining following agarose gel electrophoresis. The quality of the RNA was further assessed by the $A_{260}/A_{280}$ ratio being greater than 1.8 and the presence of the "two to one" ratio of 28s and 18s rRNA bands following agarose gel electrophoresis. The presence of only a faint high molecular weight band for each of the samples indicated a substantial removal of the genomic DNA contaminant. DNA contamination was estimated to be less than 10 ng of a possible 600 ng DNA in the 5 µl sample, or less than 2%.

It was also determined that some detergents and combinations thereof do not precipitate in solution. For example, some nonionic detergents, and combinations thereof, form stable suspensions and are easier to use.

| Detergent Type | Detergent Name | Total RNA Yield (µg) | 260/280 Ratio |
|---|---|---|---|
| Anionic | Ammonium Lauryl Sulfate | 4.9 | 2.0 |
| Cationic | Dodecyltrimethylammonium bromide (CTAB) | 6.2 | 1.93 |
| Nonionic | Tween-20 | 6.0 | 1.93 |
| Nonionic | Triton X-100 | 5.4 | 1.86 |

Example 3

RNA Purification in a 96-Well Plate Format

Reproducibility of RNA purification was tested using a 96-well plate. Human cells (K562, a lymphoblastoid cell line) were counted using a cell counter (Coulter Counter CBC-5, Coulter Electronics, Inc., Hialeah, Fla.) and collected by centrifugation in 50 ml polypropylene centrifuge tubes at 2000 g for 3 minutes. The cell pellets were frozen at −80° C. and thawed for experiments. Cells were mixed with RNA Lysing Solution described in Example 1 at a concentration of $3 \times 10^6$ cells per ml by adding the RNA Lysing Solution, then gently pipetting up and down five times to form a lysate. The lysate (0.15 ml per well) was aliquoted in to each well of a 96 well flowthrough-plate (hereto referred as the processing plate) of a Generation Capture Plate (Gentra Systems, Minneapolis, Minn., Cat. No. 200017) each of which was fitted with a polyester solid support of dimensions 15.39 mm circumference and 15 mm long (Filtrona® Filter Media R-22607, Filtrona Richmond, Richmond, Va.). The processing plate was covered with a clean, standard adhesive plate seal, following each reagent addition following centrifugation to prevent contamination. The plate was placed on a Generation Waste plate (Part. No. 200028, Gentra Systems, Minneapolis, Minn.). The lysate was allowed to incubate with the solid support and the nucleic acids allowed to bind to the solid support for 5 minutes at room temperature, after which the plate was centrifuged at 2000×g for 3 minutes (Centrifuge Model C412 equipped with an M4 Swing-Out Rotor, catalog no. 11175338; Jouann, Winchester, Va.). A volume of 150 μl RNA wash solution (Gentra RNA Wash Solution (Part. No. S2-0025, Gentra Systems, Inc., Minneapolis, Minn.)) was added to each well, and the plate was centrifuged twice more as before. After the third wash, the waste plate was replaced with an RNase-free 96-well collection plate. A volume of 100 μl RNA elution solution (Gentra RNA Elution Solution, Part. No. S3-0025, Gentra Systems, Minneapolis, Minn.) was added to the filters and the plate incubated for 5 minutes at room temperature. The RNA was then collected by centrifugation at 2000×g for 5 minutes. To estimate RNA yield and quality, optical density (OD) at 260 nm was measured on a 96-well UV plate reader (SpectraMax Plus UV Plate Reader, Softmax Pro Version 2.2.1 software, Molecular Devices, Sunnyvale, Calif.). RNA yield was calculated as described in Example 2. RNA yields were 8.79+/−1.49 ug (17% coefficient of variation).

To judge the suitability of RNA purified using the reagents and methods of the present invention for quantitative RT-PCR, and the reproducibility of RNA yields from 96 replicate isolations, human beta-actin mRNA was amplified using the 5'-nuclease ("Taqman") assay using an ABI PRISM 7900HT Instrument (Applied Biosystems, Foster City, Calif.). A single-step reverse-transcription PCR (Taqman EZ RT-PCR Core Reagents, Cat. no. N808-0236, Applied Biosystems, Foster City, Calif.) was performed using 20 μl reactions in 384-well Optical Plates (Cat. No. 4309849, Applied Biosystems, Foster City, Calif.). A volume of 15 μl of reagent mix was added to each well of the plate, followed by 5 μl of the purified RNA (diluted 1:100 in RNase-free water). The reaction plate was maintained on ice during the reaction setup. Reactions contained 1×EZ RT-PCR Buffer, 3.0 mM manganese acetate, 0.3 mM dATP, 0.3 mM dCTP, 0.3 mM dGTP, 0.6 mM dUTP, 1× Human Beta-actin Primer/Probe Mix (VIC) (Cat. no. 4310855, Applied Biosystems, Foster City, Calif.), 0.2 Units of uracil-N-glycosylase, and 2 Units of rTth DNA polymerase. The plate was sealed with an Optical Adhesive Cover (Cat. No. 4311971, Applied Biosystems, Foster City, Calif.) and cycled as follows in the 7900HT: 50° C. for 2 minutes; 60° C. for 15 minutes; 94° C. for 5 seconds, and 60° C. for 1 minute, for a total of 50 cycles. An RNA transcript containing human beta-actin sequences was diluted from $10^{11}$ to 10 copies per reaction for use as a standard curve. During thermal cycling, the 7900HT Instrument accumulated fluorescence data during the anneal/extend phase of PCR. Data analysis was performed using Sequence Detection Systems Software (SDS version 2.0a23, Applied Biosystems). The standard curve was linear between 1000 and $10^{10}$ copies ($R^2$>0.998). Threshold cycle ($C_t$) values averaged 18.8+/−0.39 cycles (coefficient of variation=2.1%, N=96). Cycle threshold was defined as the cycle numbers at which the fluorescent amplification product was significantly greater than background. Calculated copy numbers averaged 4.6× $10^8$+/−1.0×$10^8$ copies per reaction (coefficient of variation=22%, N=96). This experiment demonstrated the consistency of beta actin transcript detection in a 96 well plate format.

Example 4

Evaluation of Purified RNA in an RT-PCR Assay

To further evaluate the suitability of the purified RNA for use in downstream analyses, RNA performance in an RT-PCR assay was assessed. RNA was reverse-transcribed in 15 μl reactions containing 5 μl of RNA purified following the procedure of Example 1, 1× GeneAmp PCR Buffer II (part no. N808-0010, Applied Biosystems, Foster City, Calif.), 0.1% Igepal CA-630 (Part no. 1-3021, Sigma Chemical, St. Louis, Mo.), 9.3 mM $MgCl_2$ (Part no. M-1028, Sigma), 1.25 mM of each of dATP, dTTP, dCTP, and dGTP (Nucleotide Set, Part no. 77100, US Biochemical, Cleveland, Ohio), 5 mM dithiothreitol (Part no. D-9779, Sigma), 2.5 ng random primers (part no. C1181, Promega, Madison, Wis.), 16 Units recombinant ribonuclease inhibitor (rRNasin, part no. N2515, Promega, Madison, Wis.), and 40 Units MMLV-RT (part no. M1705, Promega, Madison, Wis.). Reactions were incubated at 25° C. for 10 minutes to allow annealing of random primers, 42° C. for 15 minute., then at 99° C. for 5 minutes to inactivate reverse transcriptase. PCR mix was added, and amplification carried out for 5 cycles of 92° C. for 5 seconds, 64° C. for 30 seconds, 72° C. for 1 minute and 25 cycles of 94° C. for 5 seconds, 64° C. for 30 seconds, 72° C. for 1 minute, followed by a final extension at 72° C. for 15 minutes. Reactions contained 20 mM Tris-sulfate, pH 9.0, 20 mM ammonium sulfate, 0.1% Igepal CA-630, 300 nM each primer BA-F 5'-GCCAACCGCGAGAAGATGAC; BA-R: 5'-CCGTCACCGGAGTCCATCAC synthesized by Keystone Division of BioSource, Foster City, Calif., and 2.5 Units Taq DNA polymerase (Promega, Madison, Wis.). These PCR primers generate an amplicon of 134 base pairs from beta-actin mRNA. Reaction products were analyzed by electrophoresis on 2% agarose gels (100V 1 h) containing 0.5 ug/ml ethidium bromide. Bands were visualized by UV transillumination. Products of the expected size were observed.

To further assess the RNA quality, larger amplicons were readily amplified from isolated RNA using other primer sets. If RNA were substantially degraded, the larger amplicons would not be detected using standard gel electrophoreses methods. For example, a set of PCR primers from tryptophanyl tRNA synthetase mRNA (F: 5'-CCAGGGAACCCAG-CACCTAC; R: 5'-AAAGCCACAGGCGATGATGTC each synthesized by Keystone, Foster City, Calif.) were used successfully to amplify t a 492-base pair fragment from 10 samples of total RNA isolated by the present invention.

Example 5

Use of a Chaotropic Agent Reduce Effectiveness of RNA Lysing Solution

Guanidinium salts are among the most potent known inactivators of RNases. Thus, it was of interest to discover if potent chaotropes such as guanidinium isothiocyanate (GITC) and guanidinium hydrochloride could either substitute for lithium chloride or increase RNA yields using the reagents in the method of the present invention.

Three sets of experiments were conducted. The experimental conditions are as follows: (1) solid supports pre-treated with GITC; (2) cells pre-lysed in GITC, and then added to the solid support; and (3) the addition of chaotropes to the RNA Lysing Solution of Example 1. In all experiments, the solid support of Example 1 (Filtrona® Filter Media Lot No. R-20653, Filtrona Richmond, Inc. (Richmond, Va.)) was used.

In the first set of experiments, the solid supports were coated with RNA Lysing Solution or a GTIC lysing solution (Buffer RLT, Qiagen, Valencia, Calif.) by pipeting 200 µl of the solution onto the filter, then drying at 68° C. for 18 hours. Treated solid supports were tested in duplicate for their ability to purify RNA from K562 cells following the method in Example 2. Agarose gel electrophoresis of the purified RNA showed that the yield of RNA using GITC lysing solution (Buffer RLT, Qiagen, Valencia, Calif.) was less than 10% of the yield of RNA observed when the RNA Lysing Solution of the present invention was used to bind to the filter as described in Example 2.

The second set of experiments attempted to evaluate the ability of GITC to facilitate binding of RNA to the solid support. K562 cells were lysed in Buffer RLT (Qiagen, Valencia, Calif.), then applied to an untreated filter. Binding in the presence of Buffer RLT gave significantly lower yields, less than 50% of RNA using RNA Lysing Solution as described in Example 1.

Lastly, chaotropic salts were added to the RNA Lysing Solution of the invention to evaluate the ability of chaotropic salts to improve RNA yields in the method of the present invention. RNA Lysing Solution of the present invention as described in Example 1, to which was added 4 M guanidinium isothiocyanate, 6M guanidinium hydrochloride, or 8.3M urea was used to purify RNA according to the method described in Example 1. It was determined that the pH of each of the aforementioned solutions were 8.8. 8.8, and 8.6 respectively. RNA yields obtained using the urea-LiCl Lysing Solution were about 35% of the RNA yields using the RNA Lysing Solution of Example 1. Even less RNA was recovered using guanidinium hydrochloride, and no RNA was observed on the gel when guanidinium thiocyanate was added to the RNA Lysing Solution. These results demonstrate that guanidinium salts can neither substitute for lithium salts nor potentiate the effect of RNA binding in the presence of lithium salts. Thus, these experiments show that RNA binding to the present solid support in the presence of lithium chloride occurs by a distinctly different mechanism from the binding of nucleic acids to similar solid phases in the presence of chaotropic salts Example 6

Effect of Low pH on RNA Purification Using a Solid Support

RNases are rapidly and efficiently inactivated at low pH. Hence, it was of interest to determine if the present method could be enhanced by the use of a low pH RNA Lysing Solution.

Thus, two RNA Lysis Solutions were prepared, one at low pH (pH 4.6) and a second at high pH (pH 8.8) according to Example 2 of the present invention, except that the 45 mM Tris pH 8.8 buffer was replaced by 45 mM Citrate buffer pH 4.6. A 300 µl volume of each RNA Lysis Solution was added to a solid support (Filtrona Lot # R 20653, Filtrona Richmond, Inc. (Richmond, Va.)) and dried as described as in Example 2. Following the RNA purification method from Example 2 the quantities of recovered RNA were determined by UV spectrophotometry. The average yield of RNA purified using pH 4.6 RNA Lysis Solution was 3.60 ug (standard deviation was 0.86 with 4 replicates) while the average yield using pH 8.8 RNA Lysis Solution was 11.40 ug (standard deviation was 0.32 with four replicates). The results showed that reducing the pH of the Lysis Solution significantly reduced the yield and purity of the resulting RNA.

Example 7

Determination of Genomic DNA Contamination in Purified RNA Samples

It is desirable for gene-expression and other analysis that RNA preparations be substantially free of DNA to give consistent and reliable results. Genomic DNA contamination is a problem with many current RNA purification technologies. It was of interest to assess the genomic DNA content of purified RNA purified by the reagents and method of the current invention.

Two assays were employed to assess genomic DNA content: real time quantitative PCR and agarose gel electrophoresis. In the first assay, DNA content was estimated from RNA purified in a 96 well format as described in Example 3. Genomic DNA content of the purified RNA was estimated with a quantitative assay using a Taqman RNase P assay. The single-copy human RNase P gene was amplified in 20 µl reactions using Taqman Universal PCR Master Mix (Part No. 4304437, Applied Biosystems, Foster City, Calif.), the TaqMan RNase P Detector Reagents (FAM) (part no. 4316831, Applied Biosystems, Foster City, Calif.), at the following cycling conditions: 50° C. for 2 minutes; 95° C. for 10 minutes; 95° C. for 15 seconds, and 60° C. for 1 minute, for a total of 50 cycles. A dilution series of human genomic DNA (supplied with Cat. no. 4316831, Applied Biosystems, Foster City, Calif.) from 5 pg to 50 ng ($R^2$ for the standard curve >0.998) allowed calculation of ng DNA per reaction. Total nucleic acid yield was calculated at an absorbance of 260 nm assuming primarily RNA content. Average genomic DNA content of the purified RNA samples was estimated to be 0.22%+/−0.03 (S.D.) (coefficient of variation=14.7%, N=96).

In an additional experiment using real time PCR, RNA was purified from 12 samples using the column method described in Example 1 and from 12 samples using the commercially available kit (RNAeasy, Qiagen, Cat. No. 74103 (Valencia, Calif.)). In each case, RNase P values in ng DNA were expressed as a percentage of total nucleic acid (calculated from $A_{260}$–$A_{320}$ using 40 µg/ml as the conversion, assuming mostly RNA). The commercial kit produced RNA with significantly more contaminating DNA (average=7.91%+/−2.68 (S.D.) than the present invention (average=0.643%+/−0.21%). Thus, the invention represents a significant improvement over existing technology.

In the second assay, genomic DNA was estimated from agarose gel electrophoresis of purified RNA. In RNA purified by most commercial kits such as the aforementioned kit, genomic DNA is clearly visible as a band migrating more slowly than the 28s rRNA band. RNA purified by the present invention was observed to contain significantly less genomic DNA than the aforementioned kit. In some RNA preparations obtained using the reagents and methods of the present invention, no genomic DNA band was visible. This data shows that the reagents and methods of the present invention yield RNA of significantly higher purity than some currently available commercial kits.

Example 8

Use of Purified RNA for Microarray Analysis

Total RNA was purified from 10 million K562 cells using the method of the invention according to the procedure described in Example 1, using an RNA elution solution volume of 20 µl to generate more concentrated RNA. The RNA was fluorescently-labeled with Cy3- and Cy5-dCTP using the CyScribe™ First-Strand cDNA Labelling Kit (Amersham Pharmacia, Piscataway, N.J., Cat. No. RPN 6202) using a quantity of 20 ug RNA for each dye. The fluorescently-labeled cDNA was hybridized to the GeneMAP™ Human 384×5 Test Chip (Genomic Solutions, Ann Arbor, Mich., Cat. No. S9700102) following the method described by the manufacturer. After a 16 hour hybridization, the microarray was scanned using the ScanArray 5000 microarray analysis system (Packard Bioscience, Meriden, Conn., Cat. No., 900-3011523001). The resulting microarray images demonstrated strong signal at both the Cy3 and Cy5 excitation wavelengths with very low background fluorescence. To estimate the background, GenePix™ Pro 3.0 analysis software (Axon Instruments, Inc., Foster City, Calif.) was used to determine signal-to-noise ratios. Ratios were calculated for 24 grids with 16 spots per grid, where each spot was compared to the perimeter region immediately surrounding it. Negative spots were not included in the analysis. A positive hybridization signal is defined by the manufacturer as being greater than 3 fold over background. In this experiment, the mean signal-to-noise ratios for both Cy3 and Cy5 excitation wavelengths were well above that level, at 7.015 and 10.678 respectively, indicating very low background fluorescence from high quality RNA.

Example 9

Evaluation of RNA Quality Using bioAnalyzer

To assess the quality of RNA purified using the reagents and methods of the present invention, RNA samples were analyzed using an Agilent 2100 bioAnalyzer (Agilent Technologies, Palo Alto, Calif.). This system may be used to assess the size and quality of the major ribosomal RNA bands generating an electropherogram and calculating the ratio between the 28s and 18s peak areas. Generally, two resolvable peaks with ratios greater than 1.5 indicate that the RNA sample is undegraded.

RNA from a total of $50 \times 10^6$ K562 cells was purified according to the protocols described in Example 1 with the exception that the RNA lysis volumes were 500, 750 and 1000 respectively, and RNA elution volumes were 20, 60, and 100 µl. Following purification, 1 µl of each RNA sample was loaded into a well of an RNA LabChip® (Agilent Technologies, Palo Alto, Calif.) prepared in a reagent supplied by the manufacturer and according to the manufacturer's instructions. Following electrophoresis, the resulting electropherogram was examined. All samples showed two distinct 28s and 18s peaks. The average 28s to 18s ratio was 2.46, with a range of 1.89 to 3.53 for all samples. The ratios were thus all greater than 1.5, indicating that the method of the present invention generated substantially undegraded RNA.

Example 10

Purification of Viral RNA from Human Plasma

RNA was purified from human plasma infected with the hepatitis C virus (HCV). Both treated and untreated filters were used as described in Example 2 and 1 respectively. Treated filters (Filtrona® Filter Media (Lot. No. R-20653)) were prepared by pipetting 0.2 ml of RNA Lysing Solution onto each filter in a Spin-X carrier tube, then heating at 68° C. for 12-18 hours in a laboratory oven. Plasma (0.2 to 0.4 ml) was applied to the treated filter, and RNA was allowed to bind for 5 minutes at room temperature. The filter was washed as described in Example 1. RNA was eluted in a 150 µl volume of RNA elution solution (Gentra RNA elution solution, Part. No. S3-0025, Gentra Systems, Minneapolis, Minn.).

Untreated solid supports were used to purify RNA from a 200 µl sample of human plasma. RNA Lysing Solution was mixed with the human plasma at ratios of between two to six, and the entire sample was applied to the solid support with exogenous nucleic acid (10-30 µg of human total cellular RNA per isolation obtained from K562 cells). The solid support was then washed and eluted, following the method described in Example 1. The addition of the exogenous carrier RNA was found to improve yields significantly, by at least 50% over conditions in which no carrier RNA was used.

To determine whether HCV RNA was purified, an HCV specific RT-PCR was performed. Primers specific to a 241 base target in the 5'-untranslated (5'-UTR) region of HCV were used. Reverse transcription was performed in 30 µl reactions containing 10 µl of RNA, 1×PCR Buffer II (Cat. No. N808-0010, Applied Biosystems), 5.8 mM MgCl$_2$, 1.25 mM each of dATP, dTTP, dCTP, and dGTP (Nucleotide Set, Cat. no. 77100, US Biochemical), 5 mM dithiothreitol (Cat. no. D-9779, Sigma Chemical Co. (St. Louis, Mo.)), 2.5 ng random primers (Cat. no. C1181, Promega, Madison, Wis.), 20 Units recombinant RNase inhibitor (rRNasin, Cat. no. N2515, Promega), and 40 Units MMLV reverse transcriptase (part no. M1705, Promega Madison, Wis.). Reactions were incubated at 25° C. for 10 minutes to allow annealing of random primers, 42° C. for 15 minutes for cDNA synthesis, then at 99° C. for 5 min. to inactivate reverse transcriptase. PCR amplification was conducted in 50 µl reactions containing 5 µl cDNA, 1× Taqman Universal PCR Master Mix (Cat. No. 4304437, Applied Biosystems, Foster City, Calif.), 400 nM forward primer (5'-GCAGAAAGCGTCTAGCCATG-GCGTTA, synthesized by Keystone Division of BioSource, Foster City, Calif.), 400 nM reverse primer (5'-GCAAGCAC-CCTATCAGGCAGTACCACAA, Keystone), and 200 nM 6FAM-labelled probe (5'-TAMRA-CATAGTGGTCTGCG-GAACCGGTGAGT-6FAM-3', synthesized by Synthegen, Houston, Tex.). The plate was heated as follows in an ABI PRISM 7900HT Instrument (Applied Biosystems, Foster City, Calif.): 50° C. for 2 minutes; 95° C. for 10 minutes; 94° C. for 5 seconds, and 60° C. for 1 minute for 50 cycles. Data were collected during the anneal/extend phase of PCR and analyzed using Sequence Detection System software (SDS)

version 2.0. Amplification was observed using RNA purified from plasma RNA using both treated and untreated filters.

Example 11

Purification of RNA from Whole Blood

Whole blood samples were collected from three donors in 10 ml Vacutainer® Brand blood collection tubes (EDTA K3 No. 16852, Becton Dickinson, Franklin Lakes, N.J.) and stored at 4° C. until use. White cell counts were determined using a Coulter Counters® CBC-5 (Coulter Electronics, Inc. Hialeah, Fla.) calibrated using CBC-7 Hematology Controls (R&D Systems, Minneapolis, Minn.). A volume of 200 ul was removed and combined with 600 ul RBC Lysis Solution (Gentra Systems, Inc., Minneapolis, Minn.) in a 1.7 ml microfuge tube. After incubating for three minutes at room temperature to lyse the contaminating red blood cells, the white cells were pelleted by centrifuging at 12,000×g for 20 seconds. The supernatant fraction containing the lysed red cells was removed and the pellet was rinsed with 300 ul RBC Lysis Solution to further remove contaminants. The white blood cells were suspended in RNA Lysis Solution and the RNA purified according to Example 1. Beta globin transcripts were amplified using a one step reverse transcriptase PCR amplification kit (rTth Amplification Kit Cat. No. n808-0098 PE Biosystems, Foster City, Calif.) according to the manufacturer's instructions. The primer sequences were F 5' TAG CCA CAC CAG CCA CCA CTT TCT-3' and R 5' CCT GGC TCA CCT GGA CAA CCT CAA-3'. The purified RNA was amplified using the cycling conditions of 60° C. for 30 minutes, 94° C. for 3 minutes followed by 30 cycles of 94° C. for 1 minute, 70° C. for 1 minute, 72° C. for 1 minute and then completed by incubating for 7 minutes at 72° C. To determine whether the RNA isolated using the present invention was of sufficient purity to be reverse transcribed into cDNA and then amplified, 5 of the 50 µl amplification reaction were analyzed by 2% agarose gel electrophoresis for 60 minutes at 80 volts. The gel image showed a strong band at the expected size of 194 base pairs for each duplicate and for each of the three RNA donor samples, indicated substantially pure starting RNA template material. In addition, amplification from contaminating genomic DNA would have generated a fragment of approximately 1000 base pairs. Since no amplification product of this size was observed on the gel, no substantial genomic DNA contamination was present in the purified RNA.

We claim:

1. A method for purifying RNA from biological material comprising RNA, comprising:
   (a) mixing said biological material with an RNA Lysing Solution, wherein the RNA Lysing Solution
      (i) is buffered at a pH of greater than 7,
      (ii) comprises an amphiphillic reagent and an RNA complexing salt, wherein the RNA-complexing salt is an alkali-metal salt present at a concentration greater than 4 M, and
      (iii) is free of a strong chaotropic substance;
   (b) lysing said biological material with said RNA Lysing Solution to form a lysate comprising RNA and non-nucleic acid biological matter;
   (c) contacting said lysate to an immobilized non-silica solid support, wherein said RNA in said lysate preferentially binds to said solid support;
   (d) washing said solid support with an RNA wash solution to remove non-nucleic acid biological matter; and
   (e) preferentially eluting the bound RNA from said solid support with an RNA elution solution to obtain the RNA.

2. The method of claim 1, wherein the biological material is selected from the group consisting of crude and partially purified mixtures of nucleic acids.

3. The method of claim 1, wherein the biological material is selected from the group consisting of plant cells, mycoplasma, protozoa, bacteria, fungi, viruses, yeasts, rickettsia and homogenates thereof.

4. The method of claim 1, wherein the biological material is selected from the group consisting of whole blood, bone marrow, blood spots, blood serum, blood plasma, buffy coat preparations, saliva, cerebrospinal fluid, and solid animal tissues.

5. The method of claim 1, wherein the biological material is selected from the group consisting of feces, urine, tears, and sweat.

6. The method of claim 1, wherein the biological material is selected from the group consisting of environmental samples taken from air, water, sediment and soil.

7. The method of claim 1, wherein the non-silica solid support comprises components selected from a group consisting of cellulose, cellulose acetate, nitrocellulose, nylon, polyester, polyethersulfone, polyolefin, polyvinylidene fluoride, and combinations thereof.

8. The method of claim 1, wherein the non-silica solid support comprises a polyester.

9. The method of claim 1, wherein the immobilized non-silica solid support comprises combinations of polyesters.

10. The method of claim 1, wherein the solid support is contained in a vessel.

11. The method of claim 1, wherein the RNA Lysing Solution is free of guanidinium salts and urea.

12. The method of claim 1, wherein the RNA is selected from the group consisting of messenger RNA, transfer RNA, ribosomal RNA and viral RNA, and combinations thereof.

13. The method of claim 1, wherein the alkali-metal salt is chosen from the group consisting of sodium, potassium, lithium, cesium, and rubidium salts.

14. The method of claim 13, wherein the alkali-metal salt is a lithium salt.

15. The method of claim 14, wherein the alkali-metal salt is lithium chloride.

16. The method of claim 1, wherein the alkali-metal salt is present at a concentration of between 4-10 M.

17. The method of claim 1, wherein the amphiphillic reagent is a detergent.

18. The method of claim 17, wherein the detergent is a non-ionic detergent.

19. The method of claim 18, wherein the nonionic detergent is selected from the group consisting of tweens, tritons, nomodets, and tergitols.

20. The method of claim 1, wherein the RNA Lysing Solution comprises a chelating agent.

21. The method of claim 20, wherein the chelating agent is selected from the group consisting of EDTA and CDTA.

22. A method for purifying RNA from biological material, comprising:
   (a) contacting a biological material containing RNA with a solid support pre-treated with an RNA Lysing Solution to release RNA and non-nucleic acid biological matter and cause the released RNA to preferentially bind to said solid support, wherein the RNA Lysing Solution
      (i) is buffered at a pH of greater than 7,
      (ii) is bound to the solid support, (iii) comprises an amphiphillic reagent and an RNA-complexing salt, wherein the RNA-complexing salt is an alkali-metal salt present at a concentration greater than 4 M, and
(iv) is free of a strong chaotropic substance;
(b) washing said solid support with an RNA wash solution to remove the non-nucleic acid biological materials; and
(c) preferentially eluting the bound RNA from said solid support with an RNA elution solution to obtain the RNA.

23. The method of claim 1, wherein the RNA that is purified is substantially undegraded RNA.

24. The method of claim 10, wherein the vessel is a centrifuge tube, spin tube, syringe, cartridge, chamber, multiple-well plate or test tube.

25. The method of claim 22, wherein the biological material is selected from the group consisting of crude and partially purified mixtures of nucleic acids.

26. The method of claim 22, wherein the biological material is selected from the group consisting of plant cells, mycoplasma, protozoa, bacteria, fungi, viruses, yeasts, rickettsia and homogenates thereof.

27. The method of claim 22, wherein the biological material is selected from the group consisting of whole blood, bone marrow, blood spots, blood serum, blood plasma, buffy coat preparations, saliva, cerebrospinal fluid, and solid animal tissues.

28. The method of claim 22, wherein the biological material is selected from the group consisting of feces, urine, tears, and sweat.

29. The method of claim 22, wherein the biological material is selected from the group consisting of environmental samples taken from air, water, sediment and soil.

30. The method of claim 22, wherein the solid support is a non-silica solid support.

31. The method of claim 30, wherein the non-silica solid support comprises components selected from the group consisting of cellulose, cellulose acetate, nitrocellulose, nylon, polyester, polyethersulfone, polyolefin, polyvinylidene fluoride, and combinations thereof.

32. The method of claim 30, wherein the non-silica solid support comprises a polyester.

33. The method of claim 22, wherein the immobilized non-silica solid support comprises combinations of polyesters.

34. The method of claim 22, wherein the solid support is contained in a vessel.

35. The method of claim 22, wherein the RNA Lysing Solution is free of guanidinium salts and urea.

36. The method of claim 22, wherein the RNA is selected from the group consisting of messenger RNA, transfer RNA, ribosomal RNA and viral RNA, and combinations thereof.

37. The method of claim 22, wherein the alkali-metal salt is chosen from the group consisting of sodium, potassium, lithium, cesium, and rubidium salts.

38. The method of claim 37, wherein the alkali-metal salt is a lithium salt.

39. The method of claim 38, wherein the alkali-metal salt is lithium chloride.

40. The method of claim 22, wherein the alkali-metal salt is present at a concentration of between 4-10 M.

41. The method of claim 22, wherein the amphiphillic reagent is a detergent.

42. The method of claim 22, wherein the detergent is a non-ionic detergent.

43. The method of claim 42, wherein the non-ionic detergent is selected from the group consisting of tweens, tritons, nomodets, and tergitols.

44. The method of claim 22, wherein the RNA Lysing Solution comprises a chelating agent.

45. The method of claim 44, wherein the chelating agent is selected from the group consisting of EDTA and CDTA.

46. The method of claim 22, wherein the RNA that is purified is substantially undegraded RNA.

* * * * *